(12) United States Patent
Everett et al.

(10) Patent No.: US 6,179,611 B1
(45) Date of Patent: Jan. 30, 2001

(54) DENTAL OPTICAL COHERENCE DOMAIN REFLECTOMETRY EXPLORER

(75) Inventors: Matthew J. Everett; Billy W. Colston, Jr.; Ujwal S. Sathyam, all of Livermore; Luiz B. Da Silva, Pleasanton, all of CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/315,000

(22) Filed: May 19, 1999

Related U.S. Application Data (60) Provisional application No. 60/116,884, filed on Jan. 22, 1999.

(51) Int. Cl.[7] ................................................ A61C 1/00
(52) U.S. Cl. ........................................... 433/29; 128/665
(58) Field of Search ................................ 433/29, 72, 215; 128/665; 356/317, 318, 341

(56) References Cited

U.S. PATENT DOCUMENTS

| | | | |
|---|---|---|---|
| 4,858,001 | * 8/1989 | Milbank et al. | 433/29 |
| 4,883,425 | * 11/1989 | Zimble | 433/215 |
| 5,022,856 | * 6/1991 | Zimble | 433/29 |
| 5,306,144 | * 4/1994 | Hibst et al. | 433/29 |
| 5,382,163 | * 1/1995 | Putnam | 433/29 |
| 5,690,486 | * 11/1997 | Zigelbaum | 433/29 |
| 5,880,826 | * 3/1999 | Jung et al. | 433/29 |
| 5,971,755 | * 10/1999 | Liebermann et al. | 433/29 |
| 6,024,562 | * 2/2000 | Hibst et al. | 433/29 |

* cited by examiner

Primary Examiner—Todd E. Manahan
(74) Attorney, Agent, or Firm—Daryl S. Grzybicki; Alan H. Thompson (57) ABSTRACT

A hand-held, fiber optic based dental device with optical coherence domain reflectometry (OCDR) sensing capabilities provides a profile of optical scattering as a function of depth in the tissue at the point where the tip of the dental explorer touches the tissue. This system provides information on the internal structure of the dental tissue, which is then used to detect caries and periodontal disease. A series of profiles of optical scattering or tissue microstructure are generated by moving the explorer across the tooth or other tissue. The profiles are combined to form a cross-sectional, or optical coherence tomography (OCT), image.

26 Claims, 5 Drawing Sheets

DENTAL OPTICAL COHERENCE DOMAIN REFLECTOMETRY EXPLORER

A priority date for this application has been established by prior U.S. Provisional Patent Application Ser. No. 60/116,884, entitled "Dental Explorer", filed on Jan. 22, 1999.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a dental explorer device for detecting caries and periodontal disease using optical coherence domain reflectometry.

2. Description of Related Art

There are no technologies currently available for producing cross-sectional images of dental microstructure for detection of tooth decay or reliably quantifying the soft tissue changes that occur in gingivitis and periodontal diseases. Diagnoses of disease state are usually made using mechanical probing, visual or tactile examination, and radiographic imaging. Visual inspection alone is effective only for gross lesions where serious tooth decay has occurred. A common method to probe for caries, or tooth decay, is visual and tactile examination, specifically direct observation using a dental explorer. The tooth is visually examined and tactilely explored to determine the presence of indicators of tooth decay such as surface irregularities, crevices, or discoloration. However, the practice of probing all accessible tooth surfaces with a sharp explorer is coming under increased scrutiny since it can further damage enamel already weakened by decay and may also cause cross-contamination between teeth.

Since tooth decay primarily affects the region of calcium below the tooth surface, detection of caries before significant damage occurs in the tooth is very difficult. By the time caries is evident under visual and tactile examination of the tooth, the disease is usually in an advanced stage, requiring a filling and occasionally leading to tooth loss. As a consequence of conservative diagnoses and treatment, there are false positives leading to unnecessary drilling and placement of restorations in healthy teeth. Currently there is no device for accurately determining whether restorations are in need of replacement, resulting in enormous costs for unnecessary replacement of good restorations and complications such as root canals from not replacing defective or aged restorations.

Radiography is often used for detection of cavities, since it provides integrated views of tooth structure that in certain orientations can isolate carious lesions. The sensitivity of radiographic systems, however, is limited by visible changes in film density, making identification of small carious or precarious regions difficult. Since radiographs are two dimensional, precisely locating the position of such decay is impossible. Moreover, due to the orientation of the x-ray imaging, only interproximal lesions (between the teeth) are easily detected, while occlusal lesions (top of the tooth), are difficult to detect unless they are very large. In addition, radiography uses harmful ionizing radiation and provides no information on soft tissue state. Periodontal disease cannot be identified until significant bone loss has occurred.

To detect periodontal disease, mechanical probes are placed between the soft tissue and tooth to assess the condition of the tissue. The depth of probe penetration is measured, and the attachment level is estimated from a fixed reference point on the tooth. These probes can be painful for the patient and have several sources of error resulting from variations in insertion force, inflammatory status of tissue, diameter of probe tips, and anatomical tooth contours.

Given the disadvantages of current detection techniques, a need clearly exists for a device that can provide early, safe, and painless diagnosis of caries and periodontal disease. Only when the progression of caries is detected early can restorative dentistry be effective. The present invention provides such a device and applies the optical techniques of optical coherence domain reflectometry and optical coherence tomography to image dental tissue and detect the presence of caries and other problems.

Optical coherence domain reflectometry (OCDR) was developed as a high resolution ranging technique for characterization of optical components and was based on bulk optics. See Youngquist et al., "Optical coherence-domain reflectometry: a new optical evaluation technique", *Optics Letters* 12(3):158–160 (1987). The first fiber optic based OCDR system was constructed by the U.S. National Bureau of Standards for micro-optic technology. See Danielson et al., "Guided-wave reflectometry with micrometer resolution", *Applied Optics* 26(14):2836–2842 (1987).

OCDR uses a low coherence Michelson interferometer to probe the sample, generating reflection signals as a function of depth. When the probe beam is transversed across the sample, a series of axial scans can be stacked together to form a high-resolution two-dimensional optical coherence tomogram. See Lee et. al, "Profilometry with a coherence scanning microscope", *Applied Optics* 29(26):3784–3788 (1990). Optical coherence tomography (OCT) was developed to produce cross-sectional images of biological microstructure by combining transverse scanning with a fiber optic OCDR system. See Huang et al., "Optical Coherence Tomography", *Science* 254:1178–1181 (1991). U.S. Pat. No. 5,321,501 discloses the general means for construction of an OCT system, specifically as it applies to OCT imaging of the eye for diagnosis of ocular diseases. U.S. Pat. No. 5,459,570 discloses OCT imaging of biological tissue, including measurement of tissue optical properties and tissue birefringence. These OCT devices provide imaging in the eye and circulatory system.

The application of OCT for dental applications was pioneered by the University of California at Lawrence Livermore National Laboratory. U.S. Pat. No. 5,570,182 discloses the use of OCT for diagnosis of dental caries and periodontal diseases. The ability of OCT to produce in vivo images of clinically relevant biological microstructure in has been demonstrated clinically by the applicants. See Colston et al., *Optics Express* 3:230–238 (1998).

In order for OCT to be practical and convenient to clinicians for use on patients, it would be advantageous to package a hand-held, portable OCDR dental explorer or mechanical probe device for non-invasively evaluating the health of dental tissues. The present invention uses a fiber optic inserted in a standard dental explorer or mechanical periodontal probe, designed to replace conventional, non-imaging counterparts. These improved devices can safely and accurately collect in vivo, intraoral OCDR and OCT images of dental tissue and microstructure for evaluation of dental health.

SUMMARY OF THE INVENTION

This invention is a dental explorer device or mechanical periodontal probe containing a fiber optic that provides information for diagnosing the state and structure of hard and soft tissues in the oral cavity. The invention is particularly suited for detection of carious and precarious lesions, detection of periodontal disease, and evaluation of restorations. The device can also be used for detection and evaluation of other conditions in the oral cavity that require knowledge of the internal tissue microstructure, such as gingivitis or oral cancer. The sensing capability of the dental explorer device is based on optical coherence domain reflectometry (OCDR) and optical coherence tomography, which provide the dental clinician with profiles of optical scattering as a function of depth in the tissue.

The dental explorer device contains one or more optical fibers that independently couple light from the sample arm of an OCDR system to the tip of the explorer. Light from the fiber at the tip of the explorer is directed at the hard or soft tissue. The light may be directed by angle-polishing the end of an optical fiber, or alternatively by using small diameter optics, such as gradient index lenses and prisms. The light reflected or scattered from the tissue is then collected by the same optical fiber and detected by the OCDR system, providing a single point profile of optical scattering (and thus tissue microstructure) as a function of depth.

The OCDR system consists of a light source split by a beamsplitter or fiber optic coupler into a sample arm and a reference arm. Reflected or backcattered light from the tissue is collected in the sample arm and detected by heterodyning with the light in the reference arm. Only the photons in the sample arm that have traveled the same optical path length as the photons in the reference arm (within the coherence length of the source) generate a heterodyne signal. Thus, by varying the path length of the reference beam and recording the amplitude of the heterodyne signal, the OCDR system measures the scattering coefficient of the tissue as a function of depth.

A single point measurement can be made by modulating the reference arm a very short distance, i.e., less than the coherence length of the source. Alternatively, the reference arm can be modulated a significant distance (>100 microns) to create a scattering profile of the tissue as a function of depth. By moving the dental probe transversely across the tissue, the clinician obtains a series of profiles of tissue microstructure. These profiles can be combined to form a cross-sectional, or optical coherence tomography (OCT), image of the region of interest in the oral cavity.

This explorer device has a wide range of clinical applications, including the detection of caries, the evaluation of dental restorations, and the diagnoses of gingivitis and periodontal disease. The object of this invention is to provide high resolution, in vivo images of both hard (mineralized) and soft dental tissue structure. It is further an object of this invention to use optical coherence domain reflectometry and optical coherence tomography to generate depth-resolved images of the tissue. This invention provides a safe, non-invasive alternative for locating potential and actual sites of caries incursion and will improve early disease detection and treatment. The device can be used to image structural and marginal dental restoration defects before significant leakage occurs, minimizing tooth loss and decreasing the number of unnecessary replacement restorations. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a dental explorer device or mechanical periodontal probe containing an optical fiber. The device can be coupled to an optical coherence domain reflectometry (OCDR) system to create imaging capabilities. Light is directed via an optical fiber at the dental tissue, and the scattered light reflected back from the tissue is collected and measured using an OCDR optical imaging system. This addition of OCDR to the dental explorer provides the dentist with a profile of optical scattering as a function of depth in the tissue at the point where the tip of the dental explorer touches the tissue. A series of profiles of optical scattering or tissue microstructure are generated by dragging or moving the tip of the device across the tooth or other tissue. These profiles can be combined to form a cross-sectional, or optical coherence tomography (OCT), image of the internal structure of the region of interest. The light used for probing the dental tissue is in the visible or near-infrared (e.g., >700 nm), thus avoiding the ionizing radiation used in radiography.

By imaging the internal structure of the tooth enamel, tooth decay below the tooth surface can be measured, making it possible to detect precarious lesions at an earlier stage than with a conventional explorer. In addition, the ability to generate an image of the lesion reduces the guesswork involved in detection of caries, thus minimizing the unnecessary drilling and placement of restorations in healthy teeth associated with false positives. The OCDR dental explorer is able to access all surfaces of the tooth and pinpoint the exact location of the carious lesion.

An OCDR mechanical periodontal probe device can be used to evaluate soft tissue health, while maintaining the ability of conventional mechanical probes to make attachment level measurements. For example, this OCDR probe can be inserted into the periodontal pocket and used to image the sulcus (side-firing towards tooth), alveolar bone level (straight-firing), or detached gingiva (side-firing away from tooth). This probe device can also be inserted into otherwise inaccessible sites, such as those between the teeth (interproximal) or in the back of the mouth. By moving the mechanical OCDR probe across soft tissue, OCT images can also be created.

Figure 1:
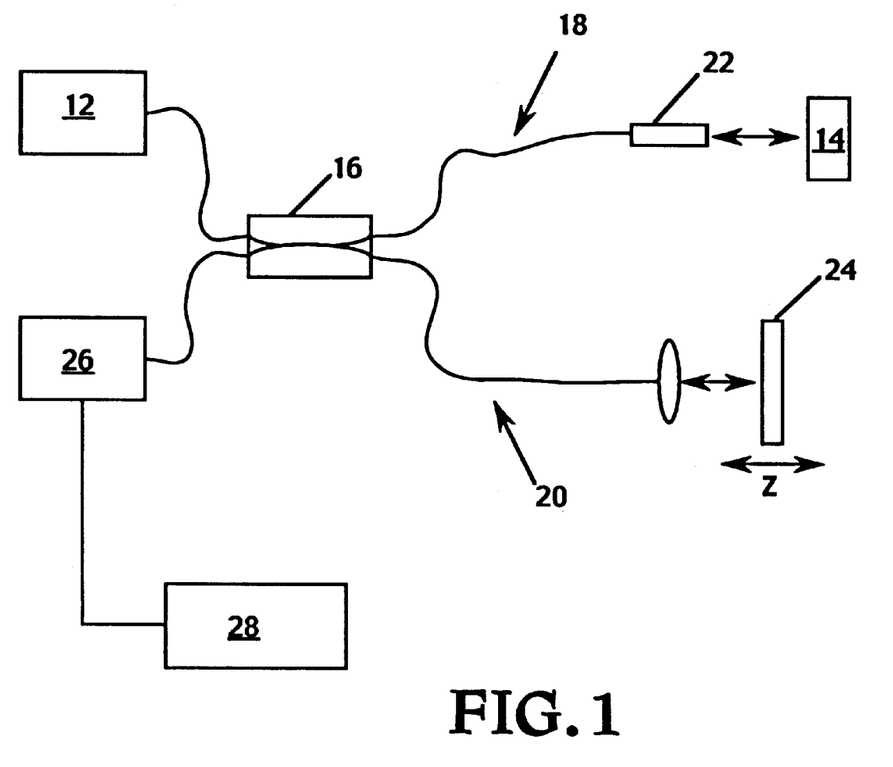
FIG. 1 shows a schematic of an optical coherence domain reflectometry system with a dental device according to the present invention.

FIG. 1 shows a schematic of a fiber optic OCDR system with a dental explorer device according to the present invention. High-resolution cross-sectional imaging is achieved by focusing light from an optical low coherence source 12 on a tissue sample 14 and measuring the intensities of the backscattered reflections as a function of axial (X) and transverse (Y) position in the tissue 14. The source 12 is typically a broad bandwidth (on the order of 50 nm) amplified spontaneous emission (ASE) source such as a superluminescent diode or fiber ASE source operating in the visible or near infrared. Light from the source 12 is split by a non-polarizing beamsplitter 16 (e.g., 2×2 fiber optic coupler) into a sample arm 18 and a reference arm 20 of a Michelson interferometer. The sample arm 18 comprises one or more optical fibers that extend into a dental explorer device 22, which is used to probe the tissue sample 14. The sample beam may pass through focusing optics before illuminating the area of interest on the sample 14. Loss in signal intensity caused by birefringence effects in the optical fiber may be corrected using polarization paddles.

The reference arm 20 provides a variable optical delay. Light input into the reference arm 20 is reflected back by a reference mirror 24, which is scanned or translated in the direction of beam propagation (Z-direction) to vary the path length. The reflected reference beam from reference arm 20 and the reflected sample beam from the sample arm 18 are recombined at the beamsplitter 16 and propagated to a photodetector 26. A data processing unit 28, typically including a demodulator, computer, and display monitor, processes the signals collected by the detector 26 using techniques well-known in the art to produce a backscatter profile or image.

The light from the source 12 is scanned axially through the tissue 14 by varying the reference arm path length. Intensity modulation associated with interference between light from the sample arm 18 and reference arm 20 reflections (heterodyning) occurs only when the optical path lengths of the two arms are matched to within the coherence length of the source 12. By varying the path length of the reference beam and recording the amplitude of the heterodyne signal on the detector as a function of path length, the OCDR system measures the amount of backscattered light from the tissue as a function of position. Thus, the intensity of backscattered light given by the amplitude of this heterodyned signal is plotted as a function of axial position in the sample, generating a one-dimensional image.

By moving or translating the sample arm 18 in one direction by moving or dragging the explorer device 22 across the dental tissue, a series of one-dimensional scans are generated. These can be combined to create a two-dimensional, cross-sectional intensity plot, which can provide depth-resolved information. Gray-scale values in the two-dimensional image correspond to backscattered intensity as a function of transverse and axial position in the tissue. The acquisition times for cross-sectional images are less than one minute, and typically on the order of seconds. Transverse scanning mechanisms are described in co-pending Hand Held Dental Imaging Device, U.S. patent application Ser. No. 60/116885, co-assigned to the same assignee, which is incorporated herein by reference. If desirable, the sample arm could be moved or translated in a second direction, normal to the first direction, to produce a three-dimensional image.

A number of possible variants of the OCDR/OCT system, including modifications for Doppler, multi-wavelength, and polarization sensitive OCDR/OCT, can be used to enhance the contrast of the dental OCT device and obtain other useful clinical information. Doppler OCDR/OCT, which provides an measurement of scatterer movement as a function of axial position, can be used to quantify internal blood flow in the gingival tissue and is potentially an indirect method for assessing soft tissue vitality. Doppler OCDR/OCT is described at Chen et al., "Noninvasive imaging of in vivo blood flow velocity using optical Doppler tomography", *Optics Letters* 22:1119–1121 (1997).

Multi-wavelength OCDR/OCT makes use of multiple wavelengths to spectroscopically resolve tissue microstructures based on their wavelength dependent absorption or scattering properties. A multiple-wavelength OCT system is described in "Multiple-Wavelength Spectroscopic Quantitation of Light-Absorbing Species in Scattering Media", U.S. patent application Ser. No. 09/008,234, assigned to the same assignee. Polarization sensitive OCDR/OCT measures the polarization state of the backscattered light, providing information about birefringence and scattering properties of the tissue.

Figure 2A:
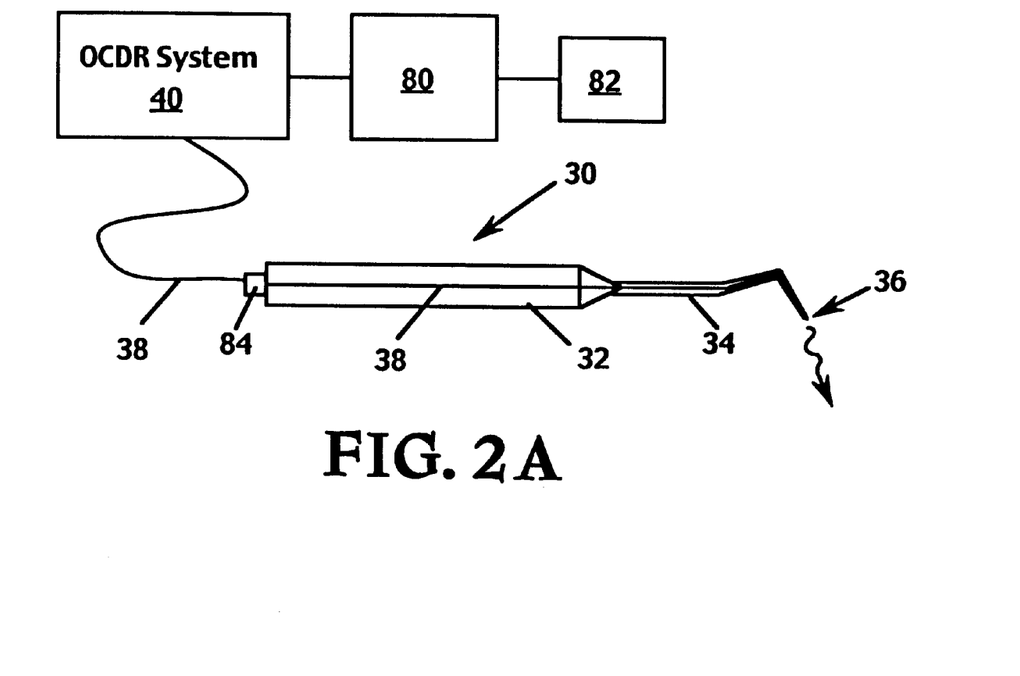
FIG. 2A shows a single fiber dental OCDR device according to the present invention.

FIG. 2A is an embodiment of a hand-held fiber optic OCDR dental explorer device 30 according to the present invention. The device 30 comprises a hand-held portion 32 so that the operator can manually manipulate the device, and a probe portion 34 that can be easily inserted into a patient's mouth. The device can be designed so that the probe is manipulated robotically or remotely, in which case a handle for an operator is unnecessary. The shape of the probe portion 34 is designed to comfortably access as much of the oral cavity as possible, and thus may be curved or angled like conventional dental explorers or periodontal probes (devices familiar to dental clinicians) so that the tip 36 of the probe reaches the posterior portions of the dental cavity. The bends or curves in the probe and optical fiber 38 are limited by the radius of curvature at which significant amounts of light escape from the fiber, typical approximately 0.5 cm.

The device 30 contains an optical fiber 38, which independently couples light from the sample arm of the OCDR system 40 to the tip 36 of the explorer device 30. The optical fiber may be a single mode or polarization maintaining (PM) fiber. The device 30 serves as an extension of the sample arm of the OCDR system 40. Light is emitted from the tip 36 of the device 30 from the distal end of the fiber 38. The OCDR system 40 provides depth-resolved detection of carious lesions wherever the tip of the explorer device 30 touches a tooth. The probe portion 34 may be detachable from the hand-held portion 32 for ease of use or to be disposable. A fiber connector 84 may be connected at the end of the hand-held portion as shown, or optionally closer to the OCDR system.

Figure 2B:
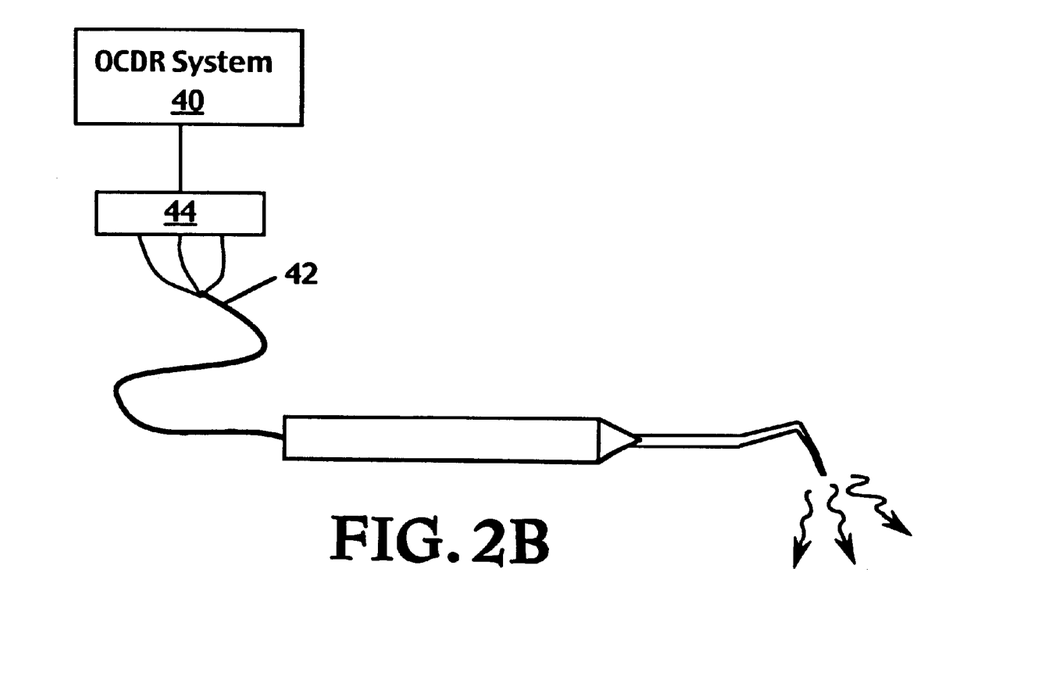
FIG. 2B shows a multi-fiber dental OCDR device according to the present invention.

Although a single optical fiber device is described in detail, the present invention can readily be modified to accommodate a multi-fiber bundle, and thus references to a single fiber also extend to the use of a plurality of fibers. For example, FIG. 2B shows an embodiment of the explorer device that contains more than one optical fiber. The light from the tip of the device is emitted from the distal end of a plurality of fibers. The fiber optic bundle 42 is connected to an optical switch 44 or optical multiplexer, which is used to switch light between the fibers in the bundle. The optical switch 44 is connected to the OCDR system 40. Alternatively, each fiber is connected to separate imaging systems 40.

Referring to FIG. 2A, the probe light emitted from the distal end of the fiber 38 is directed from the tip 36 of the explorer device 30 at or into the hard or soft tissue at the appropriate location. The probe tip 36 may be placed next to a tooth, or slipped between a tooth and periodontal tissue. The spot size is typically less than 50 μm, and can be on the order of 5–10 µm. The light may be focused and directed to the tissue via an angle-polished end of the fiber 38. The distal end of the fiber 38 is cut and/or polished at an angle, typically approximately 10 degrees, to eliminate back reflections or specular reflections from the fiber tip coupling back into the fiber. The light can also be directed to the tissue through the side of the fiber and probe by angle-polishing the fiber tip at a steeper angle, i.e., near 45 degrees, and then coating the polished surface with a reflective coating such as metal, e.g., aluminum. The probe light, which would have been emitted out the end of the fiber 78, is then reflected, thus imaging the tissue next to the fiber tip instead of in front of it.

Figure 3A:
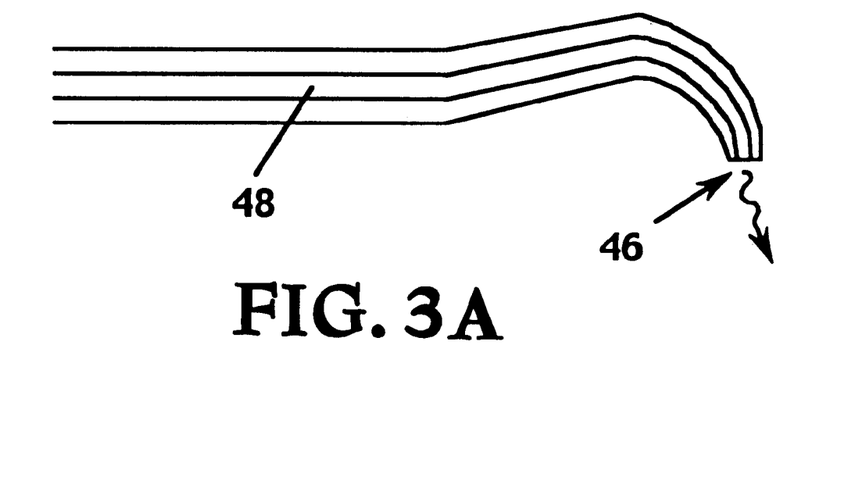
FIG. 3A shows a forward-firing embodiment of the dental device.
Figure 3B:
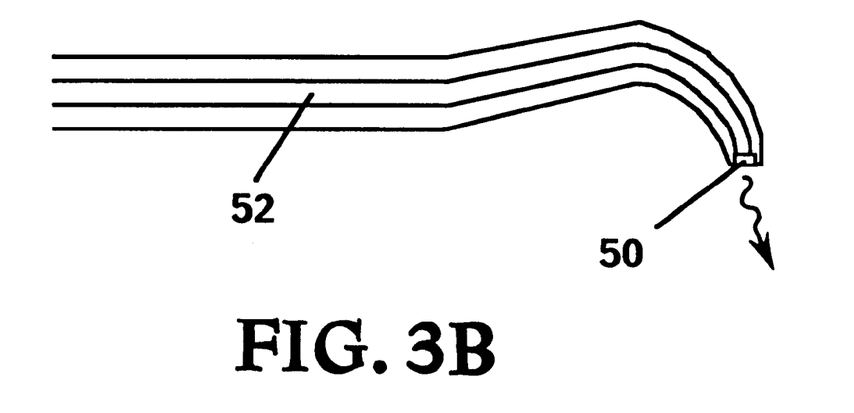
FIG. 3B shows an embodiment of the dental device with focusing/collection optics at the end of the optical fiber.

FIG. 3A shows an embodiment of the probe portion of the device with light emitted parallel from the tip 46 of the fiber 48. Alternatively, the light may be focused using one or more small diameter (e.g., submillimeter) optical elements or optics, such as gradient index (GRIN) lenses, mirrors, or prisms. FIG. 3B shows an embodiment of the probe portion of the device with focusing/collection optics 50 at the end of the fiber 52. The light may travel through free space from the fiber to the optics, or the optics may be mounted or attached directly to the fiber, as shown. If a lens is mounted to the end of the fiber, an index matching ultraviolet curable epoxy may be placed at the fiber/lens interface to minimize refractive index mismatch. The depth of focus typically extends into the tissue about 2–4 mm if the tip is held directly against the dental tissue.

The fiber and focusing/collection optics are preferably internal to the handle and probe portions of the explorer device. The probe portion may be a small diameter hollow tube, tapering like a needle at the tip, and capable of containing an optical fiber. The probe may be shaped like a conventional dental explorer, where the tip is short (e.g., 1 cm) and sharp. Alternatively, the probe can be shaped like a periodontal probe, which has a longer (e.g., 2 cm), blunt tip.

The light emitted from the end of the fiber may pass through an uncovered opening at or near the tip of the device, or through an opening covered by a window of transparent material, or the tip or probe portion may be made of a transparent material. Since the tip of the probe is in contact with dental tissues and fluids, the tip or probe portion must be detachable and disposable, or capable of being sterilized. Suitable materials for making the probe tip include glass or metals. Alternatively, a transparent, sterilized, disposable cover piece for hygienic purposes can be placed over the tip of the probe portion before insertion into the patient's oral cavity.

Figure 4A:
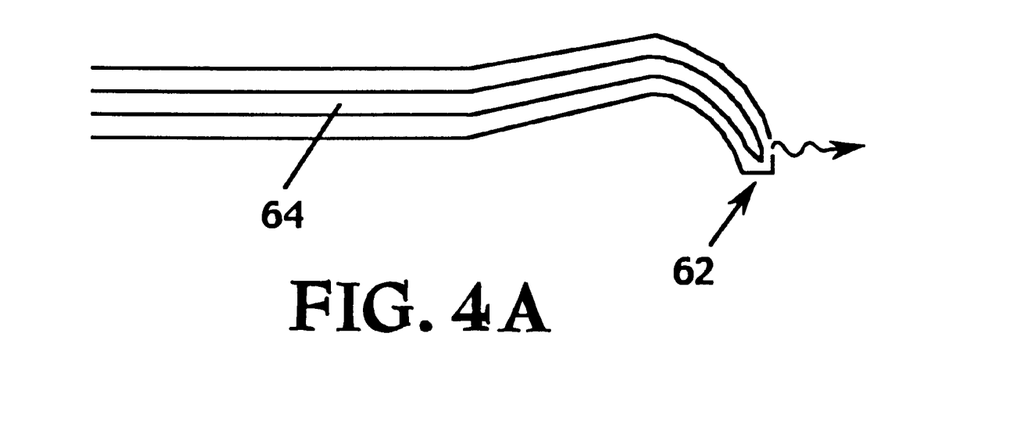
FIG. 4A shows an alternative side-firing embodiment of the present invention.

The explorer device can be constructed to enable imaging in a direction transverse to the direction of the fiber in the explorer tip. The device then directs the light at any angle or angles relative to the tip. For example, FIGS. 3A–3B show embodiments of a "forward-firing" device in which the light is emitted substantially parallel to the fiber, from the very tip of the probe portion. Alternatively, the device can be "side-firing", as illustrated in FIG. 4, where the light is emitted from the side of the tip. FIG. 4 shows an opening 60 near the tip 62 of the probe in which the light is redirected at an angle to the fiber 64 so as to be emitted transversely, or from the side.

The light may be redirected or focused to the desired location by cutting or polishing the end of the fiber 64 at an angle and coating it with a reflective surface, such as aluminum, to deflect the mode leaving the fiber. Back reflections into the fiber can be minimized by appropriate selection of the angle of the fiber face. Angles within a few degrees of 45 degrees should be avoided, as this leads to significant reflections back into the fiber.

Several prototype side-firing fibers have been designed having fibers polished at 50 degrees to normal, with the polished surface coated with aluminum. The internal mode of the fiber then reflected from the aluminum and passed into free space through the cladding of the fiber approximately perpendicular (10 degrees off) to the direction of the fiber. Light scattered from the tissue then collected in the same manner, passing through the cladding and being reflected into the core of the fiber by the aluminum coated surface. High quality OCT images were successfully generated using these fibers.

Figure 4B:
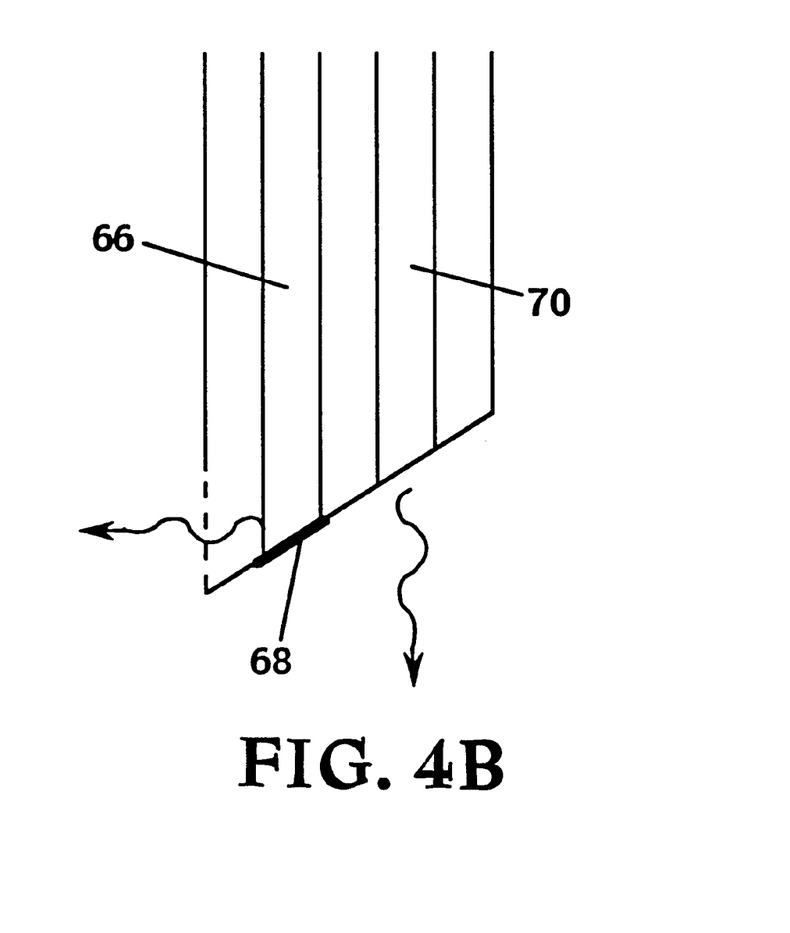
FIG. 4B shows a multi-fiber probe according to the present invention.

The angled fiber approach simplifies side viewing in OCDR/OCT systems, rather than the alternative of using small (submillimeter diameter) focusing/collection optics, such as a GRIN lens followed by an internally reflecting prism. These optics are typically attached directly to the optical fiber 64 using an index-matching epoxy. The device tip can also be designed to permit light to be emitted from one or more fibers in one or more directions at the tip or through a plurality of openings or transparent areas at or near the tip. For example, FIG. 4B shows a multi-fiber tip that is angle polished and coated so that one fiber 66 emits light from the side of the probe tip (reflected by the reflective coating 68), and the other fiber 70 emits light from the end of the tip. The cladding of the fiber (or fibers) may be removed as needed to emit light from the side of the fiber.

Referring again to FIG. 2A, after the incident beam interacts with the dental tissue, the light reflected or back-scattered from the tissue is then collected by the same optical fiber 38 and detected by the OCDR system 40. The information, i.e., the amount of scattered light, is then processed by a data analyzer 80. To serve as a tool for clinicians, the images processed by the analyzer may be displayed on a video display monitor 82 for visual inspection. Alternatively, the analyzer 80 may be programmed to send a signal when the intensity of optical scattering from the tissue is within a selected range of values, to alert the clinician that diseased tissue may be present. For example, the signal could be auditory, such as a series of beeps, or in the form of a visual display.

In the OCDR system, each measurement provides a single point profile of optical scattering (and thus tissue microstructure) as a function of depth. By moving or dragging the dental probe transversely in one direction across a tooth or other tissue, a series of profiles of tissue microstructure are generated. The collected one-dimensional scans are combined by the analyzer 70 to form a depth-resolved, two-dimensional, cross-sectional OCT image of the tooth. The probe may be used across soft dental tissues for probing gingival or periodontal problems.

Figure 5:
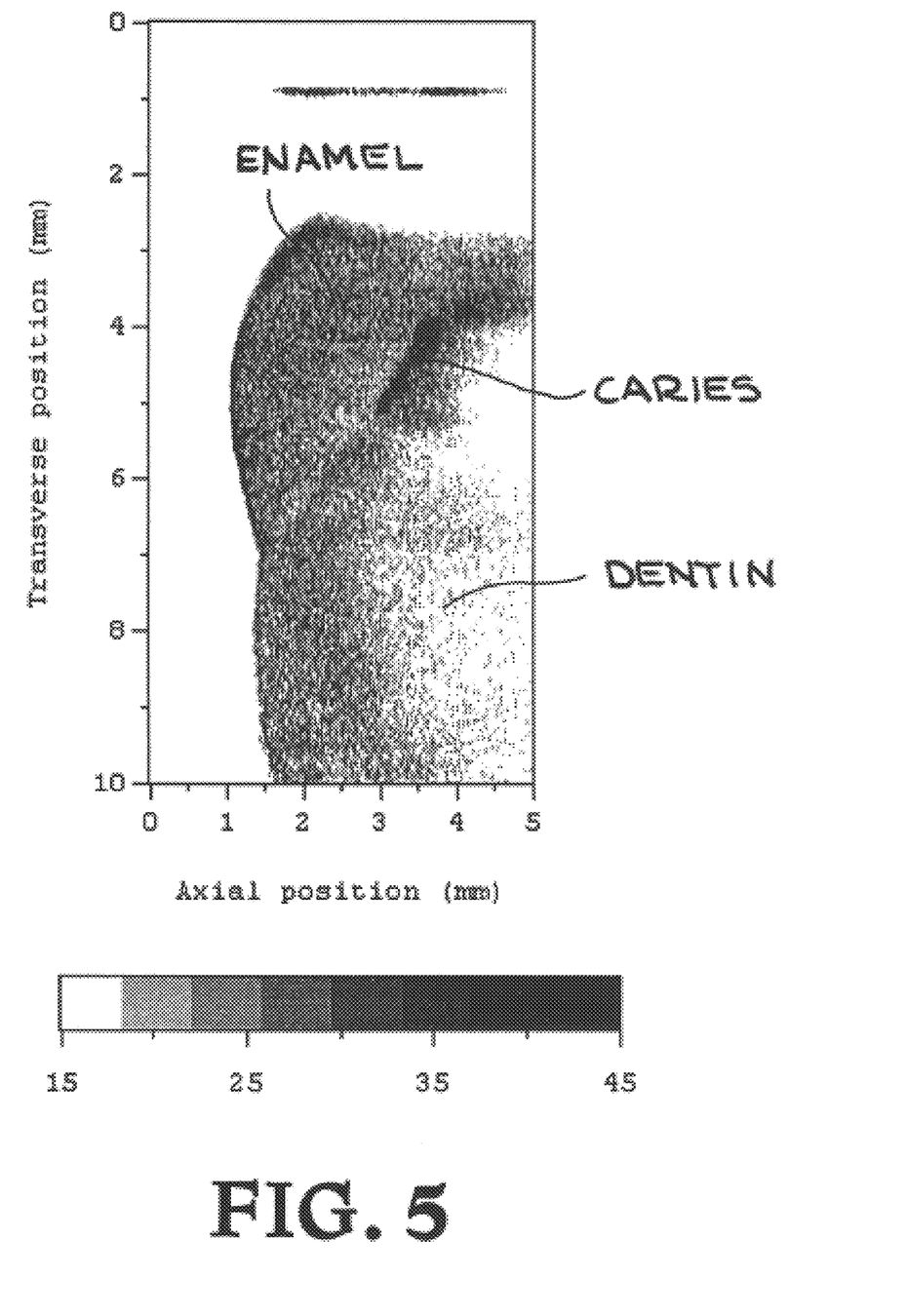
FIG. 5 shows an OCT image of an extracted carious tooth using the present invention.

FIG. 5 shows a cross-sectional OCT image of an extracted tooth containing a carious lesion, which was generated using the present invention. The OCT image was formed by combining collected profiles of the internal structure of the tooth. The gray-scale values in the two-dimensional image correspond to backscattered intensity as a function of transverse and axial position in the tissue. In this image, the dentin behind the enamel near the top of the tooth has been damaged by the lesion, leading to increased scattering, which appears as a dark region. Thus, the present invention is useful for generating images of dental tissue that can aid the dental clinician in diagnosing dental disease.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. A device for examining dental tissues, comprising:
a dental probe portion capable of being inserted into an oral cavity, wherein the probe comprises a tip and at least one single mode optical fiber having a distal end through which light is directed from the tip of the probe portion to a dental tissue of interest and through which is collected light scattered from the tissue, and wherein the fiber is capable of being connected to an optical coherence domain reflectrometry system.

2. The device as recited in claim 1, wherein the distal end of the fiber is polished at an angle.

3. The device as recited in claim 2, wherein the angle-polished end of the fiber is coated with a reflective material to reflect light transverse to the fiber.

4. The device as recited in claim 1, further comprising at least one optical element at the tip of the probe for focusing the light directed at the tissue.

5. The device as recited in claim 4, wherein the optical element is selected from the group consisting of gradient index lenses, mirrors, and prisms.

6. The device as recited in claim 4, wherein at least one optical element is attached to the distal end of the optical fiber.

7. The device as recited in claim 1, wherein the probe portion is curved.

8. The device as recited in claim 1, wherein the light is emitted parallel to the tip of the probe portion.

9. The device as recited in claim 1, wherein the light is emitted transverse to the direction of the fiber at the tip of the probe portion.

10. The device as recited in claim 1, further comprising a hand-held portion connected to the probe portion.

11. The device as recited in claim 1, further comprising a hand-held portion detachably connected to the probe portion.

12. The device as recited in claim 1, wherein the probe portion contains a plurality of optical fibers.

13. The device as recited in claim 1, wherein the light is emitted from the tip of the probe portion at a plurality of angles.

14. The device as recited in claim 1, wherein at least the tip of the probe portion is made of a material transparent to the light directed to the tissue.

15. The device as recited in claim 1, wherein at least the tip of the probe portion is made of a material capable of being sterilized.

16. The device as recited in claim 1, wherein the probe portion comprises a plurality of fibers, and further comprising an optical switch connected to the fibers.

17. The device as recited in claim 1, further comprising an OCDR system operably connected to the probe portion.

18. The device as recited in claim 17, further comprising a data analyzer operably connected to the OCDR system.

19. The device as recited in claim 18, wherein the analyzer sends a signal to a system user when scattered light collected from the tissue is within a selected range of values.

20. The device as recited in claim 18, wherein the analyzer generates an image of intensity of scattered light collected from the tissue as a function of depth in the dental tissue.

21. The device as recited in claim 18, wherein the analyzer generates an image of intensity of scattered light collected from the tissue as a function of transverse position on the dental tissue.

22. The device as recited in claim 18, wherein the analyzer generates an image of intensity of scattered light collected from the tissue as a function of depth and transverse position of the tissue.

23. The device as recited in claim 1, wherein the probe portion is selected from the dental probes consisting of dental explorers and periodontal probes.

24. A method for producing an optical coherence domain reflectometry (OCDR) image of a dental tissue of interest, comprising:
providing a dental explorer device comprising a probe portion capable of being inserted into an oral cavity, wherein the probe portion comprises a tip and at least one single mode optical fiber having a distal end, wherein the fiber is connected to an OCDR system;
positioning the tip of the probe portion at the dental tissue of interest at a point while directing light from the optical fiber at the tip of the probe portion to the tissue of interest and collecting light scattered from the tissue into the optical fiber; and
generating a profile of intensity of scattered light collected from the dental tissue.

25. The method as recited in claim 24, further comprising moving the tip in a selected direction and generating a two-dimensional optical coherence tomography image of intensity of scattered light collected from the dental tissue.

26. The method as recited in claim 24, further comprising using a plurality of wavelengths and generating color optical coherence tomography images.

* * * * *